United States Patent [19]

Nunokawa

[11] 4,422,736

[45] Dec. 27, 1983

[54] EYE FUNDUS CAMERA HAVING RING SLIT MASK IN ILLUMINATING SYSTEM

[75] Inventor: Kazuo Nunokawa, Tokyo, Japan

[73] Assignee: Tokyo Kogaku Kikai Kabushiki Kaisha, Tokyo, Japan

[21] Appl. No.: 245,149

[22] Filed: Mar. 18, 1981

[30] Foreign Application Priority Data

Mar. 21, 1980 [JP] Japan .................................. 55-36769

[51] Int. Cl.³ ........................ A61B 3/14; A61B 3/10; G03B 7/00
[52] U.S. Cl. ..................................... 351/207; 354/62; 351/214
[58] Field of Search ....................... 351/7, 14; 354/62

[56] References Cited

U.S. PATENT DOCUMENTS 3,851,954 12/1974 Kato et al. .............................. 351/7
4,102,563 7/1978 Matsumura et al. ................... 351/7

Primary Examiner—John K. Corbin
Assistant Examiner—Rodney B. Bovernick
Attorney, Agent, or Firm—Brumbaugh, Graves, Donohue & Raymond

[57] ABSTRACT

An eye fundus camera including an illuminating system having two apertured masks. One of the masks has a pair of coaxial ring-shaped slits and located with respect to the objective lens in conjugate with the cornea of the patient's eye, whereas the other has a ring-shaped slit in conjugate with the iris of the eye. The arrangement is effective to provide an increased field angle with a substantially uniform illumination without having adverse effects of harmful reflections.

4 Claims, 6 Drawing Figures

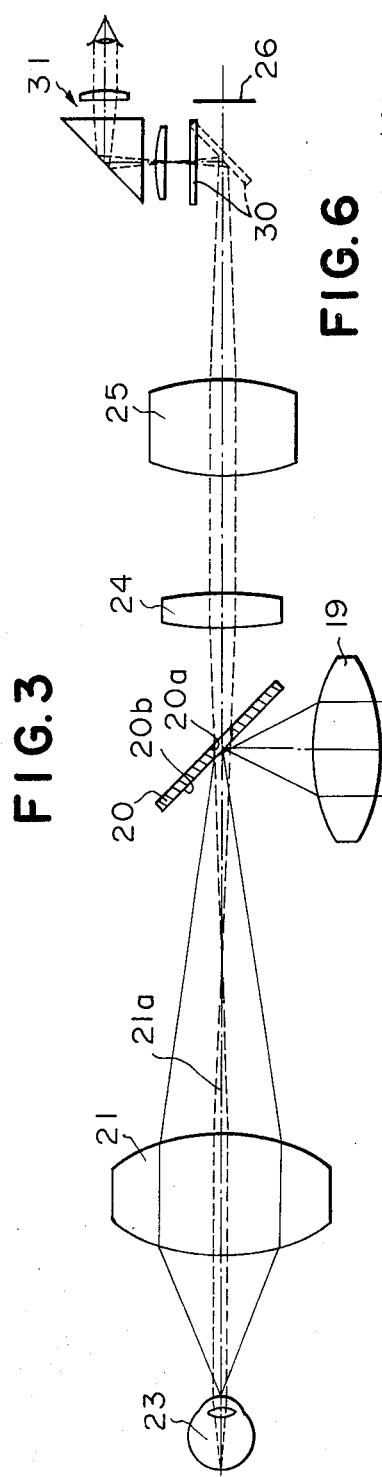
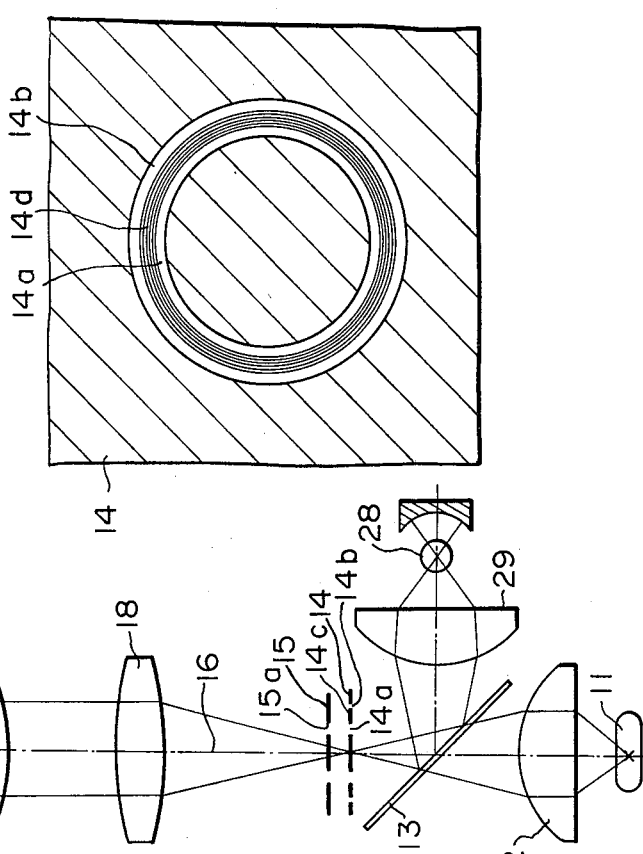
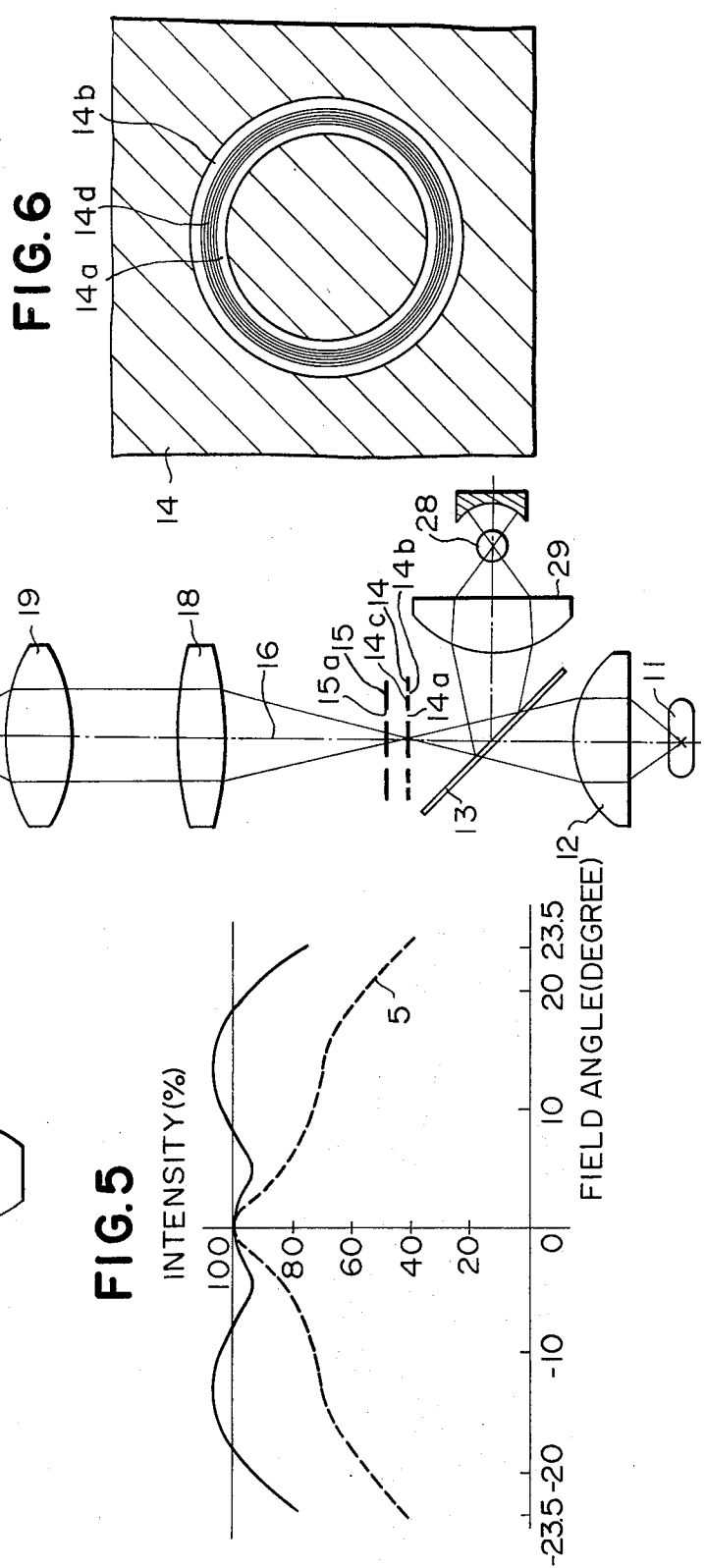

EYE FUNDUS CAMERA HAVING RING SLIT MASK IN ILLUMINATING SYSTEM

The present invention relates to an eye fundus camera and more particularly to an eye fundus camera wherein an illuminating light beam and light as reflected at the fundus of a patient's eye are both passed through common objective lens means.

In an eye fundus camera wherein an illuminating light beam is projected to a patient's eye through an objective lens which is adapted for passing the light reflected at the fundus of the patient's eye, there has been a problem of producing flares and ghost images which are caused by the illumination light reflected at the surface of the cornea and that of the eyelens. In order to prevent such harmful reflected light from passing through the objective lens to the image plane, there has been proposed to provide a illuminating optical system with a ring-shaped aperture which is substantially in conjugate with the pupil of the patient's eye with respect to the objective lens so that a ring-shaped image of the illuminating light is produced at the pupil. In the observing and photographing optical system, an aperture is provided to limit the light passing to the image plane so that the illumination light reflected at the cornea or eyelens does not overlap at the image plane with the light which has been reflected at the eye fundus and passed through the objective lens to the image plane. However, this type of arrangement is not satisfactory because it is effective to eliminate harmful reflection light only in an optical system having a relatively small field angle. In fact, actual eye fundus cameras having such optical arrangements have been designed for a field angle of approximately 30° and it has been recognized that flares and ghost images cannot be eliminated in an optical system having a field angle of 45°. The field angle may be increased without producing the problem of flares and ghost by increasing the diameter of the ring-shaped aperture. However, the solution is not preferable because an excessively large ring aperture diameter causes the illuminating light being blocked by the pupil of the eye.

Various proposals have therefore been made to solve the aforementioned problems. For example, in Japanese patent application No. 51-25413 filed on Mar. 9, 1976 and disclosed for public inspection on Sept. 10, 1977 under the disclosure number of No. 52-108123, there is disclosed an eye fundus camera wherein an image or ring-shaped illumination is produced at the front face of the eyelens and further shadows are produced respectively at the front face of the cornea and the back face of the eyelens. In Japanese patent publication No. 51-24249 published on July 22, 1976 teaches to provide a shadow for the illumination light at the front surface of the eyelens in addition to the conventional ring-shaped aperture. These proposals are indeed effective to increase the field angle without having adverse effects of harmful reflection. It should however be noted that, in the optical system as proposed in either of the above publications, it is also impossible to establish a substantially uniform illumination throughout the photographing field. In fact, the intensity of illumination is significantly decreased in the peripheral area of the field as compared with that in the central area.

It is therefore an object of the present invention to provvide an eye fundus camera in which the field angle can be increased without having adverse effects of harmful reflection of the illumination light.

Another object of the present invention is to provide an eye fundus camera in which a satisfactory illumination can be established throughout the field even under an increased field angle.

According to the present invention, there is proposed to provide apertures in the illumination system in such a manner that an image of ring-shaped illumination is produced substantially at the iris of the patient's eye and an image of a second ring-shaped illumination is produced at the corneal surface. Thus, the present invention provides an eye fundus camera comprising objective lens means adapted to be placed opposite to a patient's eye having an iris and a cornea with a distance between the objective lens means and the patient's eye, an illumination optical system for projecting an illumination light beam through said objective lens means, and an observing optical system for directing a light beam from said patient's eye through said objective lens means to an image plane, said illuminating system including a first ring-shaped aperture located substantially in conjugate with said cornea of the patient's eye and a second ring-shaped aperture located substantially in conjugate with the iris of the eye, said first ring-shaped aperture having a ring-shaped dimming band therein. According to one mode of the present invention, the dimming band is comprised of a ring-shaped opaque band so that dual ring-shaped slits are formed. In another form the ring-shaped band may be translucent or may comprise a plurality of co-axial ring slits.

The above and other objects and features of the present invention will become apparent from the following descriptions of preferred embodiments taking reference to the accompanying drawings, in which:

FIG. 3 is a diagrammatical view of an optical system of an eye fundus camera in accordance with one embodiment of the present invention;

FIG. 5 is a diagram showing the relationship between the intensity of illumination light and the field angle; and, FIG. 6 is a front view of the dual-slit aperture showing another embodiment of the present invention.

Figure 1:
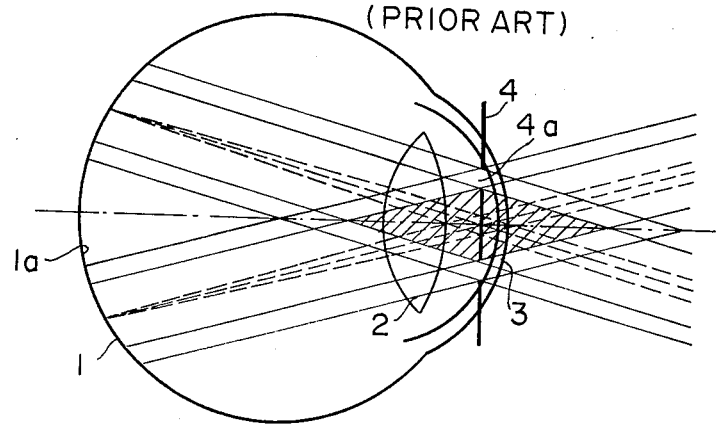
FIG. 1 is a diagrammatical view showing the paths of the illumination and observation lights in a conventional eye fundus camera.
Figure 2:
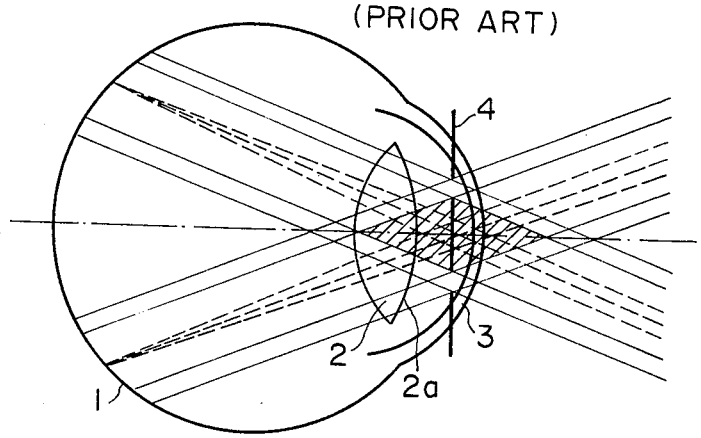
FIG. 2 is a view similar to FIG. 1 but showing the light paths under an increased field angle.

Referring now to the drawings, particularly to FIG. 1, there is schematically shown a patient's eye 1 wherein an illumination light beam is projected from a conventional eye fundus camera. An image of an apertured mask 4 is produced substantially at the pupil between the eyelens 2 and the cornea 3 so that a ring-shaped image of the illumination light 4a produced therein. Solid lines show the boundaries of the paths of the illumination light beam. The illumination light beam is reflected at the fundus 1a of the eye 1 and passes to the objective lens. The eye fundus camera has an aperture in the observing and photographing optical system so that the light beam reflected at the eye fundus 1a and passed through the objective lens to the image plane is limited to the one which passes through an optical path of which boundaries are shown by dotted lines. In FIG. 1, it will be noted that, at the surfaces of the eyelens 2 and of the cornea 3, the path of the reflected light beam is within a shadowed area where the illumination light is excluded. Thus, in this arrangement, it is possible to prevent portions of the illumination light reflected at the eyelens 2 and the cornea 3 from passing to the image plane of the observing and photographing optical system as far as the field angle is within a certain limit. However, as shown in FIG. 2, if the field angle is increased, the path of the illumination light overlaps the path of the reflected light at the surface of the eyelens 2 and possibly at the surface of the cornea. Thus, it is very possible that harmful reflections at the eyelens surface and the corneal surface be allowed to pass to the image plane to thereby produce flares and ghosts. The systems are disclosed by Japanese patent application No. 51-25413 and Japanese patent publication No. 51-24249 which have been previously discussed are considered as being effective to eliminate the above problems. However, the systems are disadvantageous in that the intensity of illumination light decreases significantly from the center to the peripheral portion of the field as shown by a curve 5 in FIG. 5.

Referring now to FIG. 3, there is shown an optical system of an eye fundus camera in accordance with one embodiment of the present invention. The eye fundus camera includes an objective lens 21 which is placed opposite to a patient's eye 23, an illumination system and an observing and photographing system. The illumination system includes a light source 11 comprised of a xenon lamp which is adapted for use in photographing and a second light source 28 comprised of a tungsten lamp which is for observation purpose. The light source 11 is associated with a condenser lens 12 which directs the light beam from the light source 11 along an illuminating optical path 16. Along the optical path 16, there are provided a first and second apertured masks 14 and 15, respectively, and lenses 18 and 19. A half-transparent mirror 13 is provided between the condenser lens 12 and the first mask 14 and a condenser lens 29 is provided between the light source 28 and the half-transparent mirror 13. Thus, the light beam from the light source 28 is directed by the mirror 13 along the illumination optical path.

The objective lens 21 has an optical axis 21a on which an apertured mirror 20 is located in such a way that the illumination light beam from the illumination system is projected through the objective lens 21 to the patient's eye 23. The first apertured mask 14 is located with respect to the objective lens 21 substantially in conjugate with the cornea of the patient's eye 23 whereas the second apertured mask 15 is substantially in conjugate with the iris of the eye 23. The apertured mirror 20 has a central aperture 20a and a ring-shaped reflective surface 20b, and is located with respect to the objective lens 21 substantially in conjugate with the pupil of the patient's eye 23.

The observing and photographing system includes relay lenses 24 and 25 for directing the light beam which has been reflected at the eye fundus and passed through the objective lens 21 to a film plane 26. A retractable mirror 30 is provided just in front of the film plane 26 to direct the light beam to an observing optical system 31.

Figure 4:
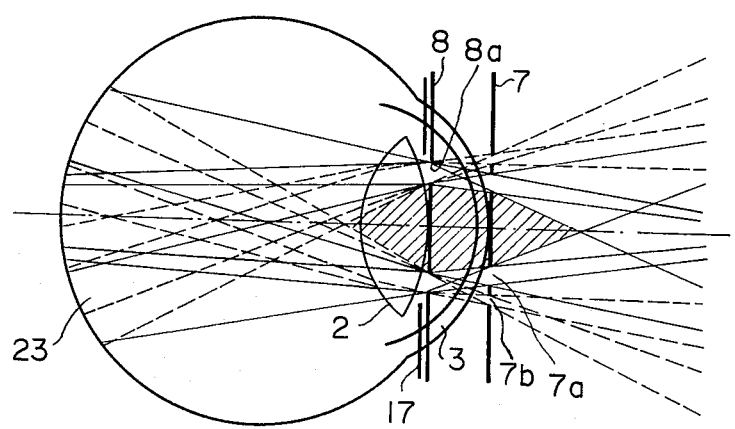
FIG. 4 is a view similar to FIGS. 1 and 2 but showing the effects of the apertures in accordance with the present invention.

Referring now to FIG. 4, it will be noted that the patient's eye 23 has an eyelens 2 and a cornea 3. Just in front of the eyelens 2, there is an iris 17. An image 7 of the first apertured mask 14 is produced on the front surface of the cornea 3 whereas an image 8 of the second apertured mask 15 is produced in substantially superposed relationship with the iris 17. The second apertured mask 15 has a ring-shaped aperture 15a so that a ring-shaped image 8a of the illumination light is produced in the image 8 of the mask 15. The first apertured mask 14 includes a ring-shaped aperture having a ring-shaped opaque band 14c so that an inner and outer ring-shaped coaxial slits 14a and 14b are formed. Thus, ring-shaped images 7a and 7b of the illumination light are produced in the image 7 of the mask 14. The opaque band 14c may be translucent so that the light passing therethrough is substantially decreased. Alternatively, the band 14c may be substituted by a plurality of ring-shaped slits as shown by 14d in FIG. 6.

According to the present invention, the first apertured mask has a dimming band 14c or 14d in the ring-shaped aperture. Therefore, the intensity of illumination in the central area of the field can be decreased with respect to that in the peripheral portion thereof. Thus, the intensity of illumination can be substantially uniformized throughout the field. In FIG. 4, the solid lines show the boundaries of the paths of the illumination light through the inner slit 14a whereas the broken lines show the boundaries of the paths of the illumination light through the outer slit 14b. It will be noted in FIG. 4, there is a sufficient shadow area around the pupil of the patient's eye, where the illumination light is excluded. It is therefore possible to obtain a wide field angle without having possibilities of producing flares and ghosts due to harmful reflections at the cornea and the eyelens.

The followings are an example of the dimensions of the slits in the apertured masks.

|  | Inner Dia. (mm) | Outer Dia. (mm) |
|---|---|---|
| First Apertured Mask |  |  |
| Inner Slit | 4.0 | 6.0 |
| Outer Slit | 7.1 | 8.1 |
| Second Apertured Mask | 4.7 | 6.9 |

The invention has thus been shown and described with reference to specific embodiments, however, it should be noted that the invention is in no way limited to the details of the illustrated structures but changes and modifications may be made without departing from the scope of the appended claims.

I claim:

1. An eye fundus camera comprising objective lens means adapted to be placed opposite to a patient's eye with a distance between the objective lens means and the patient's eye, an illumination optical system for projecting an illumination light beam through said objective lens means, and an observing optical system for directing a light beam reflected from said patient's eye through said objective lens means to an image plane, said illuminating system including a first ring-shaped aperture located substantially in conjugate with the cornea of the patient's eye and a second ring-shaped aperture located substantially in conjugate with the iris of the eye, said first ring-shaped aperture having a ring-shaped dimming band therein.

2. An eye fundus camera in accordance with claim 1 in which said dimming band is comprised of ring-shaped opaque bands located coaxially in a ring-shaped aperture so that dual ring-shaped slits are formed.

3. An eye fundus camera in accordance with claim 1 in which said dimming band is comprised of a ring-shaped translucent band.

4. An eye fundus camera in accordance with claim 1 in which said dimming band is comprised of a plurality of coaxial ring slits.

* * * * *